(12) United States Patent
Greenleaf et al.

(10) Patent No.: US 7,753,847 B2
(45) Date of Patent: *Jul. 13, 2010

(54) ULTRASOUND VIBROMETRY

(75) Inventors: James Fowler Greenleaf, Rochester, MN (US); Shigao Chen, Rochester, MN (US); Yi Zheng, Cold Spring, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 56 days.

This patent is subject to a terminal disclaimer.

(21) Appl. No.: 11/536,330

(22) Filed: Sep. 28, 2006

(65) Prior Publication Data

US 2007/0038095 A1      Feb. 15, 2007

Related U.S. Application Data

(63) Continuation-in-part of application No. 10/956,461, filed on Oct. 1, 2004.

(60) Provisional application No. 60/508,371, filed on Oct. 3, 2003.

(51) Int. Cl.
    *A61B 8/00*    (2006.01)
(52) U.S. Cl. ............................ 600/438; 73/574; 73/579; 73/587; 73/609; 600/443
(58) Field of Classification Search ................ 600/438, 600/443; 73/574, 579, 587, 609
See application file for complete search history.

(56) References Cited

U.S. PATENT DOCUMENTS

| | | | |
|---|---|---|---|
| 5,086,775 A * | 2/1992 | Parker et al. | ................ 600/453 |
| 5,606,971 A | 3/1997 | Sarvazyan | |
| 5,810,731 A | 9/1998 | Sarvazyan | |
| 5,903,516 A | 5/1999 | Greenleaf et al. | |
| 5,921,928 A | 7/1999 | Greenleaf et al. | |
| 5,974,889 A * | 11/1999 | Trantow | ...................... 73/624 |
| 5,991,239 A | 11/1999 | Fatemi-Booshehri et al. | |
| 6,068,597 A * | 5/2000 | Lin | ............................. 600/443 |
| 6,764,448 B2 | 7/2004 | Trahey et al. | |
| 6,899,680 B2 * | 5/2005 | Hoff et al. | .................... 600/449 |

(Continued)

OTHER PUBLICATIONS

Nightingale et al. (On the Feasibility of Remote Palpation Using Acoustic Radiation Force, Journal Acoust. Soc. America 110 (1) Jul. 2001, p. 625-634).*

(Continued)

*Primary Examiner*—Long V Le
*Assistant Examiner*—Ellsworth Weatherby
(74) *Attorney, Agent, or Firm*—Quarles & Brady LLP

(57) ABSTRACT

A method for measuring a mechanical property of a subject includes using an ultrasonic transducer to apply ultrasonic vibration pulses to a vibration origin in the subject in an on-off time sequence in order to impart a harmonic motion at a prescribed frequency to the subject, and when the vibration pulses are off, using the same transducer to apply ultrasonic detection pulses to a motion detection point and to receive echo signals therefrom in order to sense the harmonic motion on the subject at the motion detection point. From the harmonic signal information, a harmonic signal is detected and a characteristic such as amplitude or phase of the detected harmonic signal is measured. The mechanical property is calculated using the measured characteristic using for example a wave speed dispersion method.

19 Claims, 10 Drawing Sheets

U.S. PATENT DOCUMENTS

| | | |
|---|---|---|
| 6,951,544 B2 | 10/2005 | Trahey et al. |
| 6,984,209 B2 * | 1/2006 | Hynynen et al. ............. 600/438 |
| 2002/0007118 A1 * | 1/2002 | Adachi et al. ............... 600/443 |
| 2002/0095087 A1 * | 7/2002 | Mourad et al. .............. 600/442 |
| 2004/0167403 A1 * | 8/2004 | Nightingale et al. ........ 600/437 |
| 2004/0260180 A1 * | 12/2004 | Kanai et al. ................. 600/449 |
| 2005/0119568 A1 | 6/2005 | Salcudean et al. |
| 2005/0252295 A1 * | 11/2005 | Fink et al. ..................... 73/603 |

OTHER PUBLICATIONS

Kazuaki Michishita, et al., Ultrasonic Measurement of Minute Displacement of Object Cyclically Actuated by Acoustic Radiation Force, Jpn. J. Appl. Phys. vol. 42, 2003, pp. 4608-4612, Part 1, No. 7A, Jul. 2003, The Japan Society of Applied Physics.

* cited by examiner

Fig. 6(a)
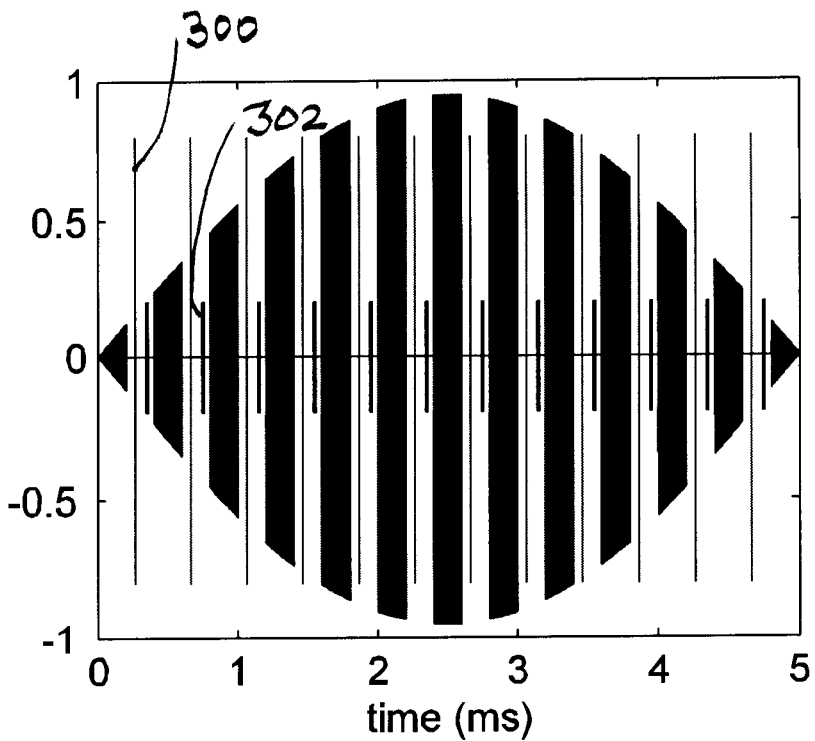
Fig. 6(b)
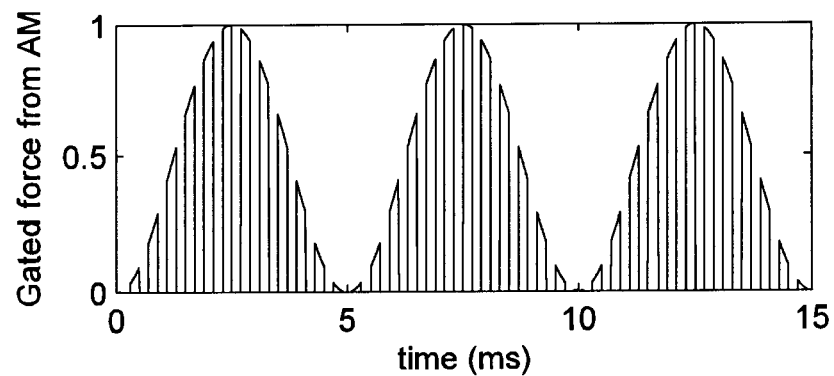
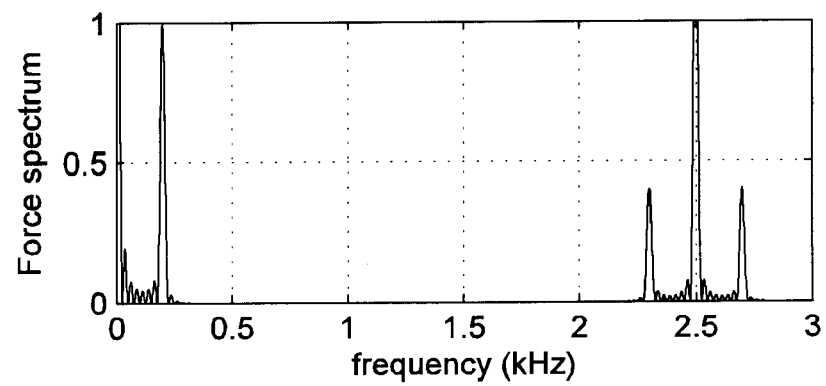
Fig. 6(c)

ULTRASOUND VIBROMETRY

CROSS-REFERENCE TO RELATED APPLICATIONS

This application is a continuation-in-part application of and claims the benefit of U.S. patent application Ser. No. 10/956,461 filed on Oct. 1, 2004 and entitled "Detection of Motion in Vibro-Acoustography", which claims the benefit of U.S. Provisional patent application Ser. No. 60/508,371 filed on Oct. 3, 2003 and entitled "Motion Detection for Vibroacoustography"; and claims the benefit of U.S. patent application Ser. No. 10/821,461 filed on Apr. 9, 2004 and entitled "Method and Apparatus For Shear Property Characterization From Resonance Induced by the Oscillatory Radiation Force", which claims the benefit of U.S. Provisional patent application Ser. No. 60/461,605 filed on Apr. 9, 2003 and entitled "Method and Apparatus For Shear Property Characterization From Resonance Induced by the Oscillatory Radiation Force".

STATEMENT REGARDING FEDERALLY SPONSORED RESEARCH OR DEVELOPMENT

This invention was made with government support under 5R01EB002640-08 and 2R01EB002167-17 awarded by the National Institutes of Health National Institute of Biomedical Imaging and Bioengineering. The government has certain rights in this invention.

BACKGROUND OF THE INVENTION

The field of the invention is coherent imaging using vibratory energy, such as ultrasound and, in particular, vibroacoustography.

There are a number of modes in which ultrasound can be used to produce images of objects. The ultrasound transmitter maybe placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing) By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction (θ) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90° sector, with each scan line being steered in increments of 0.70. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184.

Vibro-acoustography is an elasticity modality that vibrates tissue using ultrasound radiation force. The radiation force is generated by focusing two ultrasound beams on the object. These two ultrasound beams have slightly different frequencies and the tissue at the focal point vibrates at the difference frequency. The vibration frequency can be easily changed and the "stiffness" of the tissue at different frequencies can be measured. The tissue is scanned in a raster manner and its acoustic emission is detected by a hydrophone. The acquired emission data may be processed to reconstruct an image, which is related to the stiffness of the tissue. The details of the vibro-acoustography is described in U.S. Pat. No. 5,903,516 entitled "Acoustic force generator for detection, imaging and information transmission using the beat signal of multiple intersecting sonic beams" and U.S. Pat. No. 5,991,239 entitled "Confocal acoustic force generator".

A method was recently proposed to solve for the complex stiffness of a homogeneous medium or an artery by measuring shear wave speed dispersion. An oscillatory radiation force is applied to the subject using vibro-acoustography to generate shear waves of various frequencies. The speed of these shear waves is measured from shifts in phase detected over the distance propagated. Measurements of shear wave speed at multiple frequencies are then fit with appropriate theoretical models to solve for the shear elasticity and viscosity of the object as described in Ph.D. Thesis: "Direct Methods for Dynamic Elastography Reconstruction: Optimal Inversion of the Interior Helmholtz Problem", Travis Oliphant, Ph.D. May 2001 and Ph.D. Thesis: "Shear Property Characterization of Viscoelastic Media Using Vibrations Induced by Ultrasound Radiation", Shigao Chen, Ph.D. June 2002). Although the results are very promising, detection of the shear wave is achieved by an optical method, which limits its medical application because soft tissues are opaque.

SUMMARY OF THE INVENTION

One aspect of the invention is a vibro-acoustic system for measuring mechanical properties of opaque subjects such as tissue which includes an acoustic force generator that imparts harmonic motion to the subject at a prescribed frequency, an ultrasonic system for interrogating points in the subject with ultrasonic pulses and receiving echo signals therefrom which indicate the amplitude and phase of the harmonic motion at the points. The echo signals are processed to extract the harmonic motion phase information, and from this a mechanical property of the subject is calculated.

A more specific aspect of the invention is the method used to estimate the harmonic phase information in the echo signals. The echo signals are quadrature detected and the arctangent of the ratio of the Q and I components acquired at each point are calculated to produce a measured harmonic signal in slow time. The desired harmonic signal is modeled by a differential equation and the phase and amplitude parameters in this model are recursively estimated in a Kalman filter until the mean square error between the model and the measured harmonic signal is minimized.

Another aspect of the invention is a method for measuring mechanical properties of subjects such as tissue using an ultrasonic transducer to apply vibration pulses to the subject to impart harmonic motion to the subject at a prescribed frequency, and when the vibration pulses are off, using the same transducer to apply ultrasonic detection pulses to points on the subject and to receive echo signals therefrom which indicate the amplitude and phase of the harmonic motion at the points. The echo signals are processed to extract the harmonic motion phase information and from this a mechanical property of the subject is calculated.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 6(*a*) is a timing diagram of signals transmitted and received by the ultrasound system illustrated in FIG. 5 using gated AM signals for vibrating the tissue, FIG. 6(*b*) illustrates the radiation force produced using gated AM signals, and FIG. 6(*c*) illustrates the frequency spectrum of the radiation force signals;

GENERAL DESCRIPTION OF THE INVENTION

Figure 1:
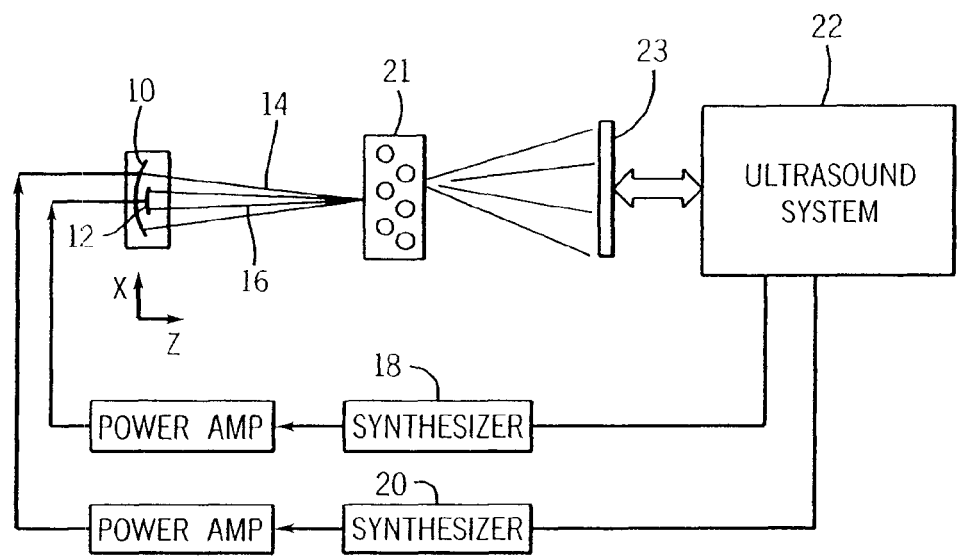
FIG. 1 is a block diagram of a vibro-acoustic system.

The present invention is a vibro-acoustic system for measuring the mechanical properties of opaque subjects such as tissue. Where the subject tissue is buried deeply beneath other tissue, optical methods for measuring the very small harmonic motions of the subject tissue cannot be used. This problem is solved by employing an ultrasonic imaging system that interrogates the subject tissue with a pulsed ultrasound beam and examines the resulting echo signals to measure the phase and amplitude of the harmonic motion imparted to the subject tissue. The challenge is to extract this information from the echo signals where the amplitude of the harmonic motion is at the submicron level.

The displacement of a point in harmonic motion of tissues can be represented in the form of, $$D(t)=D_0 \sin(\omega_s t+\phi_s) \tag{1}$$

The velocity of the motion is:

$$v(t) = \frac{dD(t)}{dt} = v_0\cos(\omega_s t + \phi_s) \tag{2}$$

where $v_0 = D_0\omega_s$.

When a pulse echo ultrasound system is focused on the tissue motion, the tissue motion is represented in the echo signals as oscillatory Doppler shifts in the received signals.

$$r(t_f, t_s) = A(t_f, t_s)\cos(\int(\omega_f + 2v(t)/c\omega_f \cos\theta)dt) = A(t_f, t_s)\cos(\omega_f t_f + \phi_f + \beta\sin(\omega_s t_s + \phi_s)) \quad (3)$$

where $t_f$ is fast time representing depth, $t_s$ is slow time representing repetitive pulses, $\omega_f$ is transmitting center frequency, $\omega_s$ is the tissue vibration frequency, $\phi_s$ is the tissue vibration phase, and $\theta$ is an angle between the ultrasound beam and direction of tissue motion. The modulation index is:

$$\beta = \frac{2v_0 \omega_f \cos(\theta)}{\omega_s c} \quad (4)$$

where c is the sound speed in the tissue.

With quadrature demodulation of the received echo signal, we have in-phase and quadrature terms:

$$I(t_f, t_s) = A(t_f, t_s)\cos(\beta\sin(\omega_s t_s + \phi_s) + \phi_f + \phi_0) \quad (5)$$

$$Q(t_f, t_s) = -A(t_f, t_s)\sin(\beta\sin(\omega_s t_s + \phi_s) + \phi_f + \phi_0) \quad (6)$$

where $\phi_0$ is a constant phase added during the quadrature demodulation to maintain $I(t_f, t_s)$ to be either all positive or all negative in slow time at a location. Thus, $$s(t_f, t_s) = -\tan^{-1}(Q(t_f, t_s)/I(t_f, t_s)) \quad (7)$$

$$y(t_s) = s(t_f, t_s) - \bar{s}(t_f, t_s) = \beta\sin(\omega_s t_s + \phi_s) \quad (8)$$

where $\bar{s}(t_f, t_s)$ is a mean value of $s(t_f, t_s)$ in slow time. If the sampling frequency in fast time is high, $I(t_f, t_s)$ and $Q(t_f, t_s)$ can be averaged with a limited length in fast time to reduce noise before $s(t_f, t_s)$ is calculated.

A bandpass filter (BPF) centered at the vibration frequency can improve $y(t_s)$ by reducing noise and distortions.

The amplitude can be directly estimated from $y(t_s)$, $$\beta = \sqrt{2}\sigma_y \quad (9)$$

where $\sigma_y$ is a standard deviation of $y(t_s)$.

The phase and amplitude in Equation (8) can be directly obtained by another quadrature demodulation at the vibration frequency in the direction of the slow time, $$I(t_s) = \beta\cos(\phi_s) \quad (10)$$

$$Q(t_s) = \beta\sin(\phi_s) \quad (11)$$

$$\beta(t_s) = \sqrt{I^2(t_s) + Q^2(t_s)} \quad (12)$$

$$\phi_s(t_s) = a\tan(Q(t_s)/I(t_s)) \quad (13)$$

The amplitude of the oscillatory Doppler shifts can also be directly measured by applying a turbulence estimation method to the $r(t_f, t_s)$ to estimate the variance of motion velocity.

In practice, the data will be noisy and have a stochastic nature. Therefore, a Kalman filter process is employed to recursively estimate the phase and amplitude. As described by R. G. Brown and P. Y. C. Hwang in "Introduction To Random Signals And Applied Kalman Filtering", 3$^{rd}$ Edition, John Wily & sons, 1997, a Kalman filter is a numerical method used to track a time-varying signal in the presence of noise. If the signal can be characterized by some number of parameters that vary slowly with time, then Kalman filtering can be used to tell how incoming raw measurements should be processed to best estimate those parameters as a function of time. In this application, a Kalman filter extracts the desired harmonic motion from random and noisy measurement data with known vibration frequency and unknown vibration amplitude and phase. Equation (8) can be represented by a 2$^{nd}$ order differential equation, $$\frac{d^2 y(t_s)}{dt_s^2} + \omega_s^2 y(t_s) = 0 \quad (14)$$

which can be transformed to a 2$^{nd}$ order state space form:

$$\begin{bmatrix} x_k(1) \\ x_k(2) \end{bmatrix} = \begin{bmatrix} 1 & 0 \\ 0 & 1 \end{bmatrix} \begin{bmatrix} x_k(1) \\ x_k(2) \end{bmatrix} \quad (15)$$

or $$x_k = \Phi x_k.$$

The measurement equation is:

$$y(t_s) = \beta\sin(\omega_s t_s)\cos\phi_s + \beta\cos(\omega_s t_s)\sin\phi_s = [\sin(\omega_s t_s), \cos(\omega_s t_s)][\beta\cos\phi_s, \beta\sin\phi_s]^T y(k) = [h_k(1), h_k(2)][x_k(1), x_k(2)]^T$$

or, $$y(k) = H_k x_k + n(k) \quad (16)$$

where $t_s = k/f_{PRF}$ and $n(k)$ is a white noise sequence having a variance R. $f_{PRF}$ is the pulse repetition frequency. Thus the amplitude and phase parameters of the desired harmonic signal can be found:

$$\beta(k) = \sqrt{x_k^2(1) + x_k^2(2)} \quad (17)$$

$$\phi_s(k) = \tan^{-1}(x_k(2)/x_k(1))$$

The estimation $\hat{x}(k)$ for $x(k)$ is given by minimizing the mean square error:

$$P_k = E[(x_k - \hat{x}_k)(x_k - \hat{x}_k)^T] \quad (18)$$

The estimated state variables in the final steps of Kalman filtering are averaged for the amplitude and phase. The filtering steps are listed below:

1. Initializing:

$$P_1^- = R, \hat{x}_1^- = E[x_1] \quad (19)$$

2. Calculating Kalman gain at k$^{th}$ step:

$$G_k = P_k^- H_k^T (H_k P_k^- H_k^T + R)^{-1} \quad (20)$$

3. Updating the state estimation:

$$\hat{x}_k = \hat{x}_{k-1}^- + G_k(y(k) - H_k \hat{x}_{k-1}^-) \quad (21)$$

4. Calculating the error covariance matrix:

$$P_k = (I - G_k H_k) P_k^- \quad (22)$$

5. Project ahead:

$$\hat{x}_{k+1}^- = \Phi_k \hat{x}_k \quad (23)$$

$$P_{k+1}^- = \Phi_k P_k \Phi_k^T + Q \quad (24)$$

where Q is zero in this application and P is an estimation error covariance matrix that describes the estimation accuracy.

The error covariance matrix provide by the Kalman filter is:

$$P = E[(x-\hat{x})(x-\hat{x})] = \begin{pmatrix} \sigma_{x1}^2 \sigma_{x2x1} \\ \sigma_{x1x2} \sigma_{x2}^2 \end{pmatrix} \quad (25)$$

where the diagonal elements represent variance of estimation errors for $x_1$ and $x_2$.

$$x_1 = \beta \cos \phi_s \quad (26)$$

$$x_2 = \beta \sin \phi_s. \quad (27)$$

The relations between the state variables and the amplitude $\beta$ and estimated phase $\phi_s$ of the harmonic motion are, $$\hat{\beta} = \sqrt{x_1^2 + x_2^2} \quad (28)$$

$$\hat{\phi}_s = a \tan x_2/x_1 \quad (29)$$

If $y = f(x_1, x_2)$ and $\sigma_{x1}, \sigma_{x2}$ are given, then the variance of y is, $$\sigma_y = \sqrt{\left(\frac{\partial f}{\partial x_1}\right)^2 \sigma_{x1}^2 + \left(\frac{\partial f}{\partial x_2}\right)^2 \sigma_{x2}^2} \quad (30)$$

For $\sigma_\beta$: $f = \sqrt{x_1^2 + x_2^2}$ $$\frac{\partial f}{\partial x_1} = \frac{\partial \sqrt{x_1^2 + x_2^2}}{\partial x_1} = \frac{1}{2}\left(\frac{1}{\sqrt{x_1^2 + x_2^2}}\right) 2x_1 = \frac{x_1}{\sqrt{x_1^2 + x_2^2}} \quad (31)$$

$$\frac{\partial f}{\partial x_2} = \frac{\partial \sqrt{x_1^2 + x_2^2}}{\partial x_2} = \frac{1}{2}\left(\frac{1}{\sqrt{x_1^2 + x_2^2}}\right) 2x_2 = \frac{x_2}{\sqrt{x_1^2 + x_2^2}}. \quad (32)$$

Therefore, the standard deviation of estimation errors of amplitude estimates is:

$$\sigma_\beta = \sqrt{\left(\frac{\partial f}{\partial x_1}\right)^2 \sigma_{x1}^2 + \left(\frac{\partial f}{\partial x_2}\right)^2 \sigma_{x2}^2} \quad (33)$$

$$= \sqrt{\left(\frac{x_1}{\sqrt{x_1^2 + x_2^2}}\right)^2 \sigma_{x1}^2 + \left(\frac{x_2}{\sqrt{x_1^2 + x_2^2}}\right)^2 \sigma_{x2}^2}$$

$$= \sqrt{\frac{x_1^2 \sigma_{x1}^2 + x_2^2 \sigma_{x2}^2}{x_1^2 + x_2^2}}$$

For $\sigma_{\phi s}$: $f = a\tan\left(\frac{x_2}{x_1}\right)$ $$\frac{\partial f}{\partial x_1} = \frac{1}{1 + \left(\frac{x_2}{x_1}\right)^2} \left(-\frac{x_2}{x_1^2}\right) \quad (34)$$

$$= -\frac{x_2}{x_1^2 + x_2^2}$$

$$\frac{\partial f}{\partial x_2} = \frac{1}{1 + \left(\frac{x_2}{x_1}\right)^2} \left(\frac{1}{x_1}\right) \quad (35)$$

$$= \frac{x_1}{x_1^2 + x_2^2}$$

$$\sigma_{\phi s} = \sqrt{\left(\frac{\partial f}{\partial x_1}\right)^2 \sigma_{x1}^2 + \left(\frac{\partial f}{\partial x_2}\right)^2 \sigma_{x2}^2} \quad (36)$$

$$= \sqrt{\left(-\frac{x_2}{x_1^2 + x_2^2}\right)^2 \sigma_{x1}^2 + \left(\frac{x_1}{x_1^2 + x_2^2}\right)^2 \sigma_{x2}^2}$$

$$= \sqrt{\frac{x_2^2 \sigma_{x1}^2 + x_1^2 \sigma_{x2}^2}{(x_1^2 + x_2^2)^2}}$$

$$= \frac{\sqrt{x_2^2 \sigma_{x1}^2 + x_1^2 \sigma_{x2}^2}}{x_1^2 + x_2^2}$$

The above equation is for the standard deviation of estimation errors of phase estimates. Thus, the Kalman filter also provides a measure of estimation quality.

The above method can be applied to estimate phase $\phi_s$ of tissue vibration propagating over a known distance $\Delta r$. Then, the shear wave speed can be estimated using the phase change $\Delta\phi_s$ over $\Delta r$:

$$c_s = \omega_s \Delta r / \Delta \phi_s \quad (37)$$

which can be used to characterize elasticity and viscosity of the tissues.

DETAILED DESCRIPTION

Referring particularly to FIG. 1, a vibro-acoustography system which employs the present invention employs an ultrasonic transducer having two elements 10 and 12 which produce two focused beams 14 and 16 that cross each other at their focal points as described in U.S. Pat. No. 5,991,239. The elements 10 and 12 are driven by respective continuous wave synthesizers 18 and 20 at ultrasonic frequencies $\omega_1$ and $\omega_2$ that differ by a desired beat frequency. The two focused beams 14 and 16 are aimed at target tissue 21 which is to be measured, and in response, the target tissue vibrates, or oscillates, at the difference frequency. These elements thus serve as a force generator which oscillates the target tissues 21 at a prescribed beat frequency.

The vibrations of the target tissue 21 are measured by an ultrasound system 22. As will be described in more detail below, the ultrasound system 22 drives an ultrasonic transducer 23 to apply a focused ultrasound beam to the target tissue 21 and to receive the echo signal reflected by the target tissue 21. The phase and amplitude of these echo signals are processed as described below to measure mechanical properties of the target tissue 21.

Figure 2:
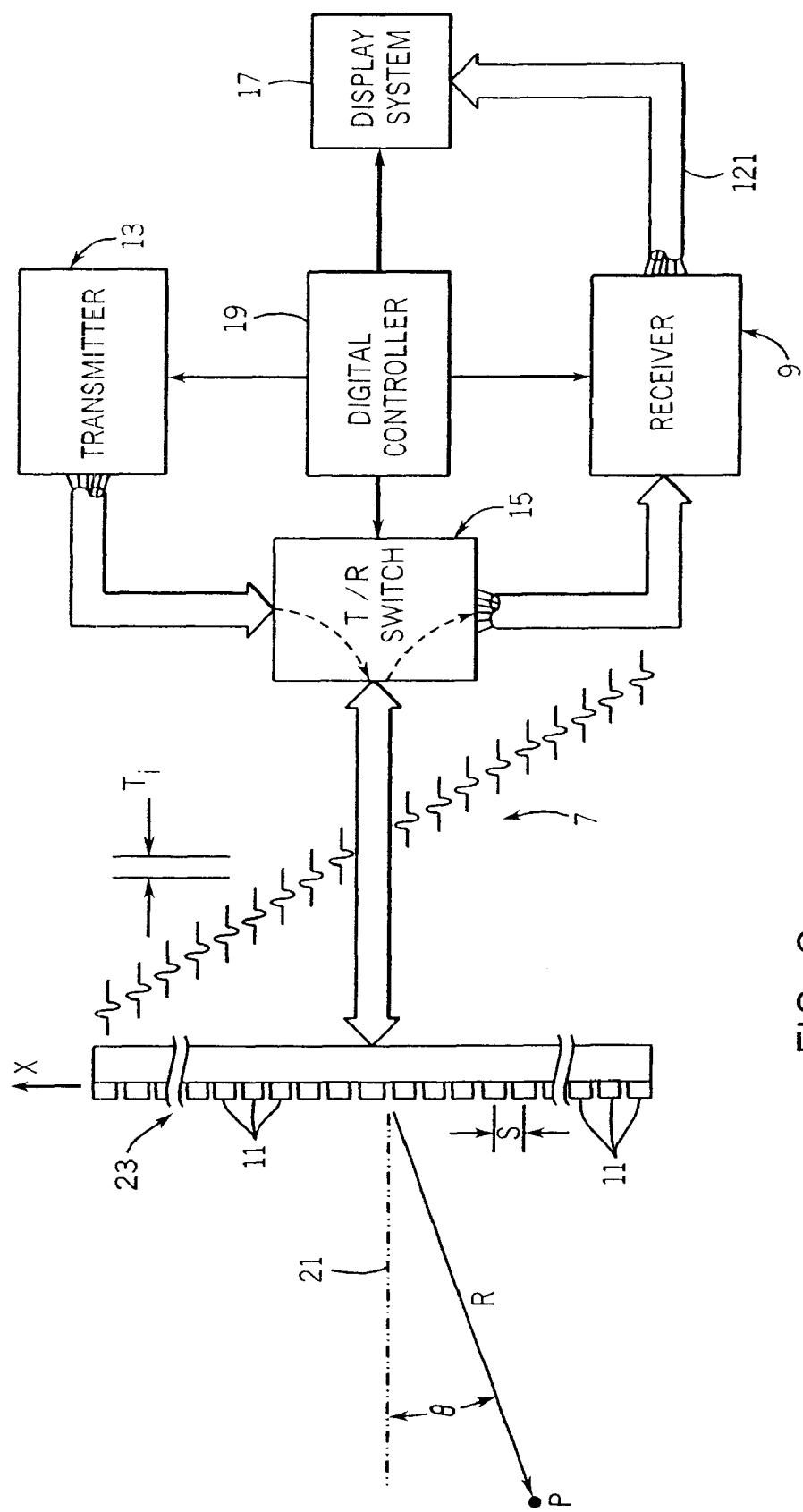
FIG. 2 is a block diagram of an ultrasound imaging system used in the system of FIG. 1.

Referring particularly to FIG. 2, a transducer array 23 is comprised of a plurality of separately driven elements 11 which each produce a burst of ultrasonic energy when energized by a pulse produced by a transmitter 13. The ultrasonic energy reflected back to the transducer array 23 from the subject under study is converted to an electrical signal by each transducer element 11 and applied separately to a receiver 9 through a set of switches 15. The transmitter 13, receiver 9 and the switches 15 are operated under the control of a digital controller 19 responsive to the commands input by the human operator. A complete scan is performed by acquiring a series of echoes in which the switches 15 are set to their transmit position, the transmitter 13 is gated on momentarily to energize each transducer element 11, the switches 15 are then set to their receive position, and the subsequent echo signals produced by each transducer element 11 are applied to the receiver 9. The separate echo signals from each transducer element 11 are combined in the receiver 9 to produce a single echo signal which is employed to produce a line in an image on a display system 17.

The transmitter 13 drives the transducer array 23 such that the ultrasonic energy produced is directed, or steered, in a beam. A B-scan can therefore be performed by moving this beam through a set of angles from point-to-point rather than physically moving the transducer array 23. To accomplish this, the transmitter 13 imparts a time delay (Ti) to the respective pulses 20 that are applied to successive transducer elements 11. If the time delay is zero (Ti=0), all the transducer elements 11 are energized simultaneously and the resulting ultrasonic beam is directed along an axis 21 normal to the transducer face and originating from the center of the transducer array 23. As the time delay (Ti) is increased, the ultrasonic beam is directed downward from the central axis 21 by an angle θ.

A sector scan is performed by progressively changing the time delays Ti in successive excitations. The angle θ is thus changed in increments to steer the transmitted beam in a succession of directions. When the direction of the beam is above the central axis 21, the timing of the pulses 7 is reversed.

Referring still to FIG. 2, the echo signals produced by each burst of ultrasonic energy emanate from reflecting objects located at successive positions (R) along the ultrasonic beam. These are sensed separately by each segment 11 of the transducer array 23 and a sample of the magnitude of the echo signal at a particular point in time represents the amount of reflection occurring at a specific range (R). Due to the differences in the propagation paths between a focal point P and each transducer element 11, however, these echo signals will not occur simultaneously and their amplitudes will not be equal. The function of the receiver 9 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle θ.

To simultaneously sum the electrical signals produced by the echoes from each transducer element 11, time delays are introduced into each separate transducer element channel of the receiver 9. In the case of the linear array 23, the delay introduced in each channel may be divided into two components, one component is referred to as a beam steering time delay, and the other component is referred to as a beam focusing time delay. The beam steering and beam focusing time delays for reception are precisely the same delays (Ti) as the transmission delays described above. However, the focusing time delay component introduced into each receiver channel is continuously changing during reception of the echo to provide dynamic focusing of the received beam at the range R from which the echo signal emanates.

Under the direction of the digital controller 19, the receiver 9 provides delays during the scan such that the steering of the receiver 9 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

By selecting proper time delays, echoes from multiple focused locations can be received to measure vibration information from several points of the tissue. The limitation of the lateral resolution of the transducer for two closely located points can be improved by assigning different transmitting codes for different locations.

The display system 17 receives the series of data points produced by the receiver 9 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display of an image.

Figure 3:
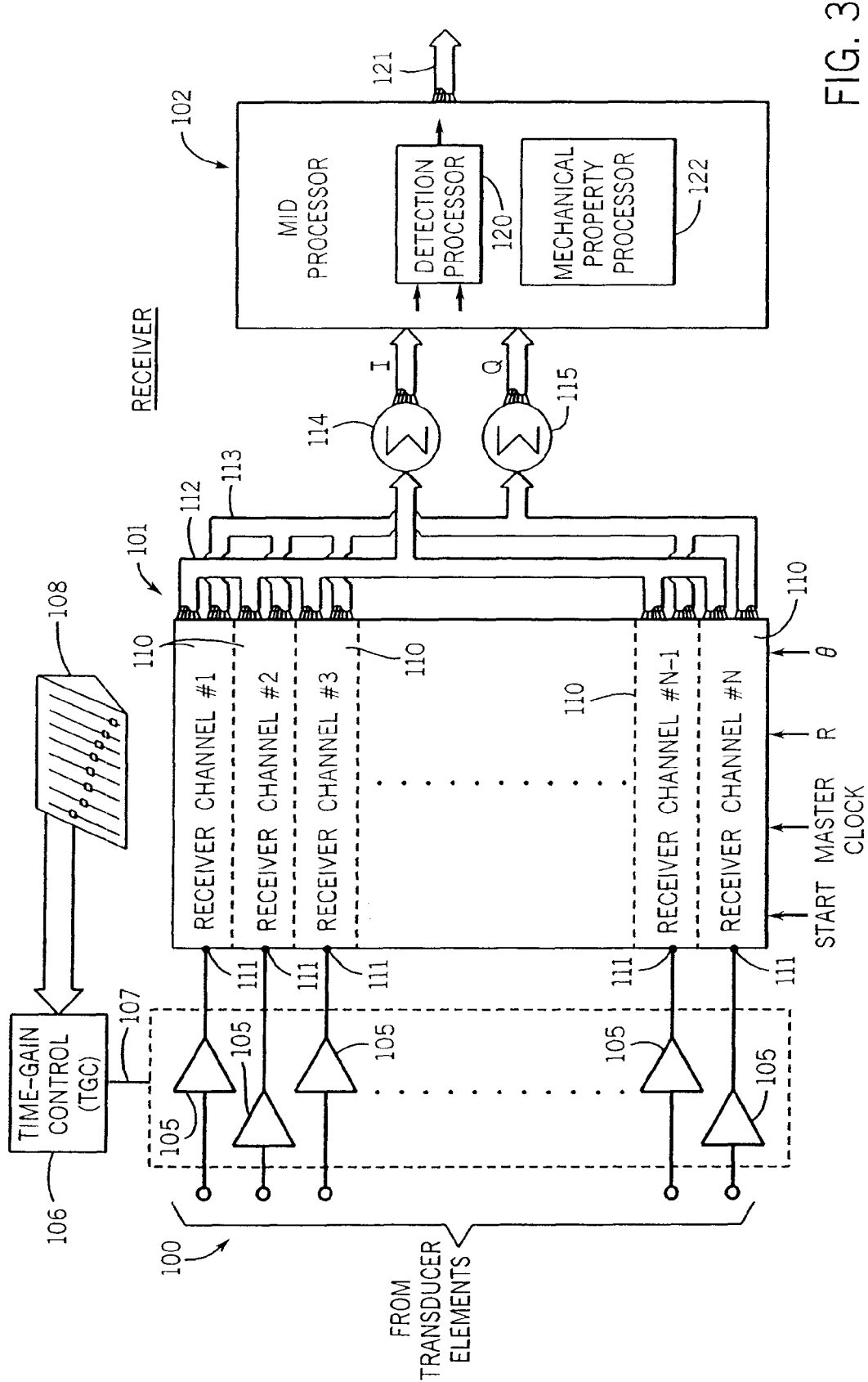
FIG. 3 is a block diagram of a receiver which forms part of the ultrasound imaging system of FIG. 1.

Referring particularly to FIG. 3, the receiver 9 is comprised of three sections: a time-gain control section 100, a beam forming section 101, and a mid processor 102. The time-gain control section 100 includes an amplifier 105 for each of the N=128 receiver channels and a time-gain control circuit 106. The input of each amplifier 105 is connected to a respective one of the transducer elements 11 to receive and amplify the echo signal which it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets TGC linear potentiometers 108 to values which provide a relatively uniform brightness over the entire range of the sector scan. The time interval over which the echo signal is acquired determines the range from which it emanates, and this time interval is divided into by the TGC control circuit 106. The settings of the potentiometers are employed to set the gain of the amplifiers 105 during each of the respective time intervals so that the echo signal is amplified in ever increasing amounts over the acquisition time interval.

The beam forming section 101 of the receiver 9 includes N=128 separate receiver channels 110. Each receiver channel 110 receives the analog echo signal from one of the TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam (θ).

For a more detailed description of the receiver 9, reference is made to U.S. Pat. No. 4,983,970 which issued on Jan. 8, 1991 and is entitled "Method And Apparatus for Digital Phase Array Imaging", and which is incorporated herein by reference.

Referring still to FIG. 3, the mid processor section 102 receives the beam samples from the summing points 114 and 115. The I and Q values of each beam sample is a 16-bit digital number which represents the in-phase and quadrature components of the magnitude of the reflected sound from a point (R,θ). The mid processor 102 can perform a variety of calculations on these beam samples, where choice is determined by the type of image to be reconstructed.

For example, a conventional ultrasound image may be produced by a detection processor 120 which calculates the magnitude of the echo signal from its I and Q components:

$$M=\sqrt{I^2+Q^2}.$$

The resulting magnitude values output at 121 to the display system 17 result in an image in which the magnitude of the reflected echo at each image pixel is indicated.

The present invention is implemented by a mechanical property processor 122 which forms part of the mid-processor 102. As will be explained in detail below, this processor 102 receives the I and Q beam samples acquired during a sequence of measurements of the subject tissue 21 and calculates a mechanical property of the tissue 21.

Figure 4:
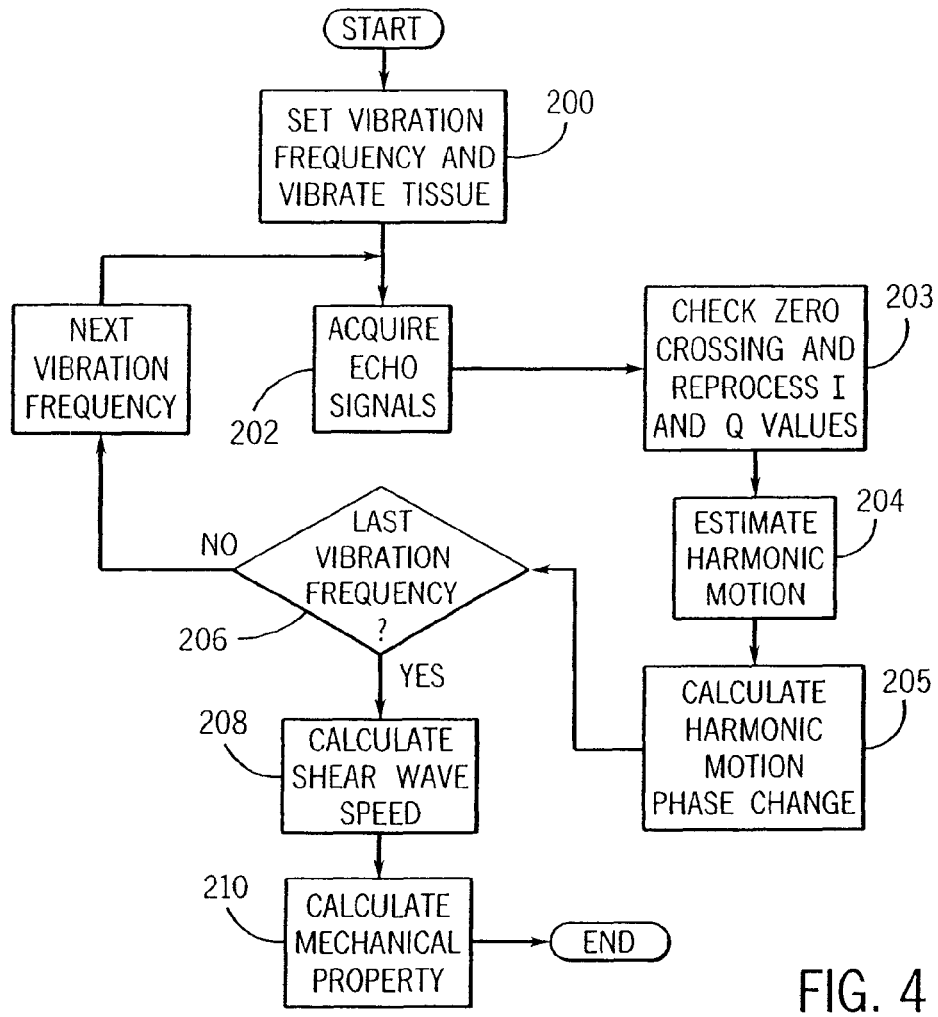
FIG. 4 is a flow chart of the steps performed by a midprocessor which forms part of the receiver of FIG. 3.

Referring particularly to FIG. 4, the mechanical property processor 122 controls the measurements made by the ultrasound system 22, the force generator elements, and it processes the resulting echo signals I and Q to satisfy equations (5) and (6) and to calculate a mechanical property of the target tissues. Such target tissues may be, for example, an artery and the mechanical property may be stiffness. The first step as indicated by process block 200 is to set the beat frequency of the force generator and excite the target tissues 21 with the force generator. As indicated at process block 202 the ultrasound system 22 is then operated to acquire echo signals from the subject tissues at a series of points. When measuring an artery, for example, 100 echoes sampled at a 40 MHz sample rate are acquired at each point, and 11 points spread evenly along 10 to 20 mm of the length of the artery are measured. Eight echo samples at the peak echo amplitude are used to obtain average I and Q values. As described above, it is necessary that all the I values remain either positive or negative in order to properly detect the harmonic signal. As indicated at process block 203, the I values are checked and if a zero crossing occurs, all the I and Q values are reprocessed to add a constant phase $\phi_0$ as indicated above in equations (5) and (6). Phase is added until no zero crossings are detected.

As indicated at process block 204, the amplitude and phase of the tissue motion at each point is then estimated from the acquired I and Q echo samples. As described above there are a number of different methods for accomplishing this, but in the preferred embodiment the arctangent of the ratio of the Q and I beam samples are calculated and the mean value is removed to obtain the harmonic motion in slow time as indicated above in Equations (7) and (8). The harmonic motion is modeled by a second order differential equation with random amplitude and phase and the known beat frequency. The amplitude and phase is then estimated in a recursive, Kalman filter process that minimizes the mean square error between the model and the measured tissue harmonic motion as indicated above in equations (14)-(18). As indicated by process block 205, the change in tissue oscillation phase as a function of distance is then calculated for this beat frequency using the calculated phase values at the 11 points along the artery.

The above process is repeated for each of the prescribed beat frequencies. When used for measuring artery stiffness, vibration frequencies of 100, 200, 300, 400 and 500 Hz are employed, and data acquisition continues until all frequencies have been acquired as determined at decision block 206.

As indicated at process block 208, the next step is to calculate the shear wave speeds in the subject tissue 21 at the different beat frequencies. Linear regression is applied to the 11 phase changed measurements to yield a phase change over 10 mm distance along the artery. From this phase change over distance information, the shear wave speed at each beat frequency is estimated as described by equation (37).

As indicated at process block 210, the final step is to calculate a mechanical property of the tissue 21 from the shear wave speed information. In the preferred embodiment the shear elasticity and viscosity of the tissue 21 is estimated from the set of shear wave speeds. These mechanical properties indicate the stiffness of the artery which is a valuable clinical measurement. This calculation is based on shear wave speed dispersion, and as described by S. Chen et al "Complex Stiffness Quantification Using Ultrasound Stimulated Vibrometry", 2003 IEEE Ultrasonics Symposium 941-944, the shear wave speeds at multiple frequencies are fit with appropriate theoretical models to solve for the shear elasticity and viscosity. For example, one appropriate equation is the so-called Voigt model:

$$c_s = \sqrt{\frac{2(\mu_1^2 + \omega\mu_2^2)}{\rho\left(\mu_1 + \sqrt{\mu_1^2 + \omega^2\mu_2^2}\right)}}$$

where $c_s$ is the shear wave speed, $\mu_1$ is the shear modulus, $\mu_2$ is the shear viscosity, $\omega$ is frequency, and $\rho$ is the density of the tissue which can be assumed to be 1000 kg/m$^3$.

While the analysis of the received echo signal is performed in the mid-processor section of an ultrasound receiver in the preferred embodiment described above, it should be apparent that these functions can also be performed in a separate processor or computer workstation.

Figure 5:
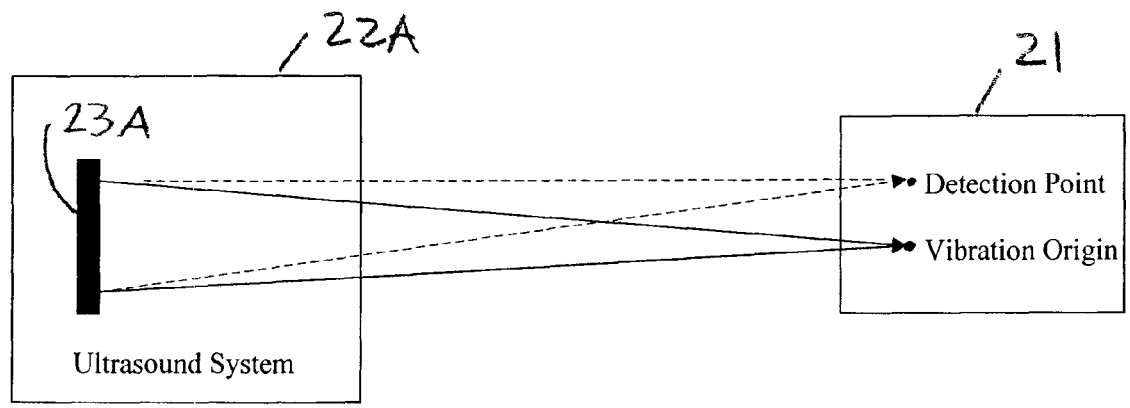
FIG. 5 is a block diagram of an ultrasound imaging system which is used to provide vibrations for target tissue to impart a shear wave and to detect the harmonic motion of the shear wave.

The system illustrated in FIG. 1 and described above requires both an ultrasonic transducer having elements 10, 12 for producing two focused beams to oscillate and impart a shear wave to the target tissue and a separate transducer 23 to detect the harmonic motion of the shear wave. As schematically illustrated in FIG. 5 however, it also possible for a single transducer 23A of an ultrasound system 22A to be used to perform both these functions to measure a mechanical property of a subject 21. In particular, transducer 23A, such as a phased array transducer, intermittently transmits a beam of ultrasonic vibration pulses (i.e., in an on-off manner) to a vibration origin on the subject to vibrate or oscillate target tissue at a prescribed frequency. During the off intervals of these vibration pulses, the focus of the transducer is electronically steered to a motion detection point at a distance R from the vibration origin and harmonic motion at that point is detected. Under the direction of the digital controller 19 (such as shown in FIG. 2) of the ultrasound system 22A, which controls the transmission and receipt of signals, a vibration mode is multiplexed with a detection mode. This enables the detection of the harmonic motion by the same transducer 23A as that transmitting the vibration pulses and both vibration and detection can be achieved without mechanically moving the transducer 23A.

Similar to the process previously described with respect to FIG. 4, the harmonic motion is detected at a motion detection point by transmitting detection pulses to the motion detection point and receiving echo pulses therefrom and then analyzing the echo pulses in the mid-processor 102 of the receiver 9. A harmonic signal is detected at the prescribed frequency in the received ultrasonic echo signals and a characteristic of the detected harmonic signal such as amplitude and/or phase is determined. The mechanical property is then calculated using the measured characteristic.

Depending on the model used to relate a measured characteristic to a mechanical property, it may be necessary to determine a measured characteristic at more than one point and/or at more than one frequency. For example, using the Voigt model requires shear wave speed to be calculated at a plurality of prescribed frequencies. Using equation (37) to calculate the shear wave speed $c_s$ requires phase measurements at two or more motion detection points.

Illustrated in FIG. 6(*a*) is a preferred time sequence of signals used to impart a harmonic motion to the subject 21 at a prescribed frequency using gated amplitude modulated (AM) signals and to detect the harmonic motion during a detection mode. Note that this graph is merely meant to illustrate when these signals occur with respect to one another since the high frequency nature (on the order of MHz) of the ultrasonic vibration pulses, ultrasonic detection pulses, and echo signals prohibits the actual delineation of these signals compared with the illustrated modulation frequency. As shown, AM ultrasonic vibration pulses generated by the ultrasound system are applied to the subject in an on-off time sequence with a detection mode occurring during the off intervals of the vibration pulses. In particular, the detection mode includes transmission of ultrasonic detection pulses at times 300 indicated by the longer vertical lines and receipt of echo signals at times 302 indicated by the shorter vertical lines.

The on phase of this sequence essentially comprises an intermittent or gated AM signal composed of ultrasonic vibration pulses that are modulated at a modulation frequency. As described in U.S. Pat. No. 5,921,928 titled "Acoustic Force Generation by Amplitude Modulating a Sonic Beam", the application of a continuous wave AM signal to a subject generates a radiation force having a frequency equal to the modulation frequency of the beam and the radiation force imparts a harmonic shear wave to the subject. Similarly, the application of a gated rather than a continuous AM signal generates a radiation force including various frequency components and a shear wave including these frequency components is imparted to the subject. FIG. 6(*b*) illustrates the radiation force resulting from the gated AM signal shown in FIG. 6(*a*). As illustrated in FIG. 6(*c*), this radiation force has frequency spectrum components at 200 Hz which is the modulation frequency, at 2.5 kHz which is the gating frequency, and other frequencies centered around 2.5 kHz. For harmonic motions, displacement of the subject is equal to its acceleration divided by the square of its vibration frequency. Therefore, even though the accelerations are comparable at both frequencies, the displacement at 200 Hz will be at least 100 times higher than that at 2.5 kHz and will dominate the displacement spectrum. In addition, higher frequency shear waves will attenuate more quickly when traveling outwards from the vibration origin. The result is that the radiation force from a gated AM ultrasound beam is also capable of providing shear waves at a prescribed frequency.

Figure 7:
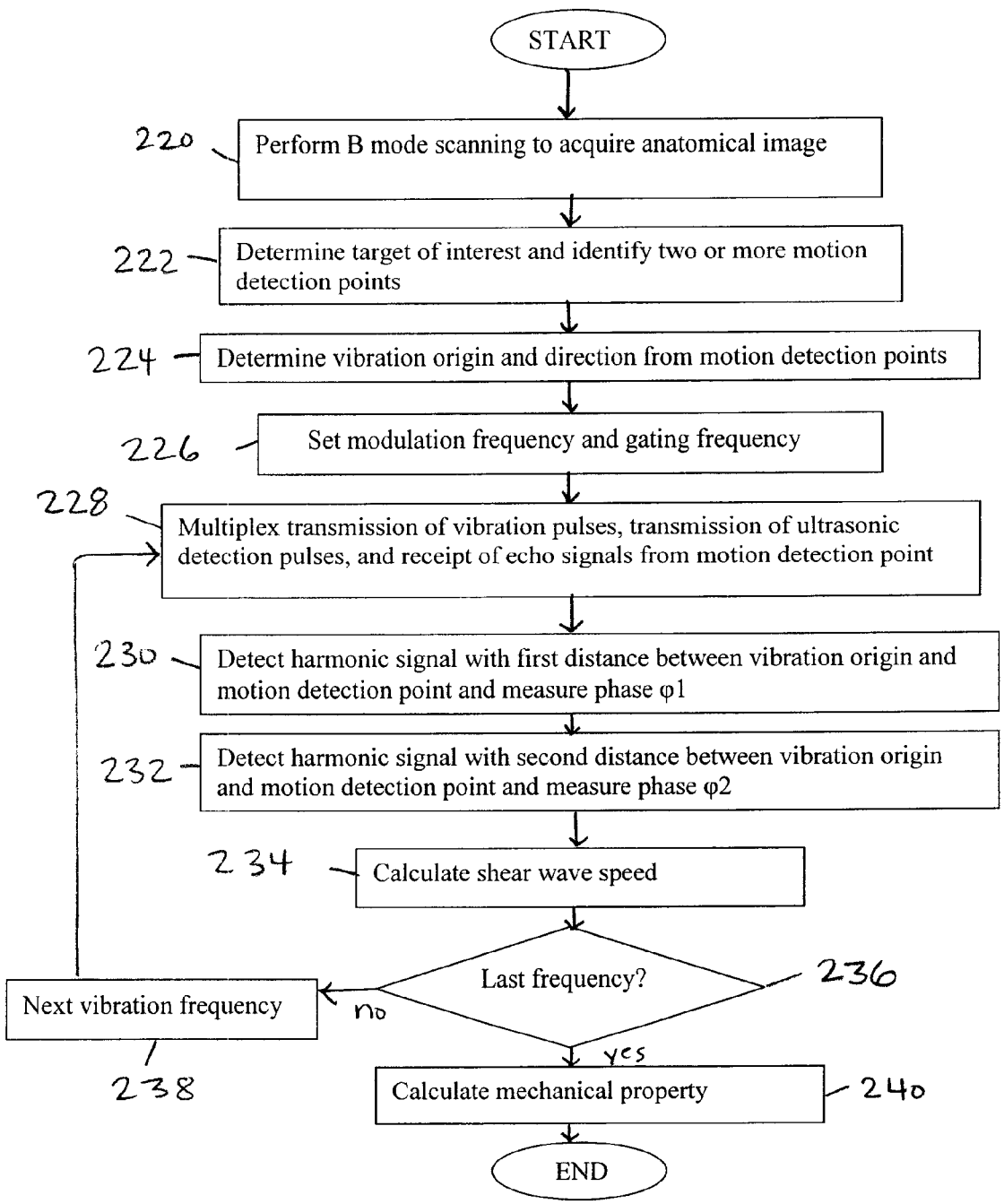
FIG. 7 is a flow chart of steps using the ultrasound imaging system of FIG. 5 to measure one or more mechanical properties of tissue such as shear elasticity and shear viscosity using a shear wave speed dispersion technique and gated AM signals for vibrating the tissue.

FIG. 7 illustrates a flow chart for measuring mechanical properties such as shear elasticity and shear viscosity of subject tissue using a shear wave speed dispersion technique and gated AM ultrasonic force pulses. In a preferred embodiment, subject tissue is analyzed and in this manner, a "virtual biopsy" is performed. For example, this method may be useful in the grading of liver fibrosis, perhaps eliminating the need for an actual liver biopsy.

In particular, as indicated process block 220, the ultrasound system 22A is operated using B mode scanning to acquire an anatomical ultrasound image of a region of interest, such as the liver. As indicated at process block 222, next a target of interest is determined such as by identifying in the ultrasound image two or more motion detection points at which it is desired to obtain the mechanical properties, assuming that the tissue is approximately homogenous at these two points. At process block 224, a vibration origin is also determined by determining a distance R between it and one of the motion detection points, with a distance of R+Δr between it and the other motion detection point. In a preferred embodiment, the vibration origin and the two or more motion detection points are co-linear. Further, the direction between a motion detection point and a vibration origin can also be selected which for a 1D transducer would amount to a selection between left or right, while for a 2D transducer array, could be selected from a range of 360 degrees.

These selections can be provided to the ultrasound system in a variety of ways such as for example by entering data, using a display to select among options, or using a touch screen or selector on an ultrasound image screen.

As previously described herein, the shear wave speed dispersion technique makes use of an estimation of wave speed using equation (37) which includes a phase difference, such that the phase $\phi_s$ of the echo signals is determined at two or more points. In a preferred embodiment, this is achieved using a single vibration origin and two different motion detection points each located a different distance from the vibration origin. It is also possible to use a single detection point and change the vibration origin. As previously discussed, more than two points can be used and the slope of a best fit line can be calculated to be used instead of a simple phase difference, but this would increase the data acquisition time.

The determination of a desired distance R between a vibration origin and a motion detection point and the determination of a desired distance Δr between the two motion detection points can be based on a consideration of the type of tissue that is under examination. For example, an appropriate distance R in the liver may be on the order of one centimeter, while an appropriate distance R for a breast lesion may be on the order of five millimeters. The outgoing shear wave generated at the vibration origin using AM pulses can be approximated as a cylindrical shear wave. Its amplitude decreases as the wave propagates outwards from the excitation center due to both geometry effect (distribution of energy over a larger cylindrical surface) and attenuation of the medium. Therefore, it is desirable to have the detection points close to the vibration origin to get higher vibration amplitude. On the other hand, locations too close to the vibration origin will be subject to the near field effect and thus the phase of the shear wave will deviate from a linear relationship with the traveled distance as assumed in Equation (37). This near field effect increases for stiffer tissue. For example, computing the phase change of a propagating cylindrical shear wave, it has been found that for a medium such as cirrhosis liver with an elasticity around 20 kPa and viscosity around 5 Pa·s, Equation (37) is valid when the detection points are at least a couple of millimeters away from the vibration origin. Additionally, according to Equation (37), speed estimation over larger Δr results in a smaller percentage error, assuming similar uncertainty in the phase measurement Δ$\phi_s$. However, Δr can not be too large; otherwise the vibration amplitude will be too small for reliable phase estimation. Therefore, the precision of shear wave dispersion characterization can be improved by optimizing the position and range of vibration detections, which may be dependent on the type of tissue under evaluation.

As indicated at process block 226, the gating frequency and the modulation frequency of the ultrasonic pulses are determined. For example, in one embodiment, the gating frequency is 2.5 kHz and a prescribed modulation frequency for a first shear wave speed is 100 Hz.

As indicated by process block 228, the transmission of the intermittent AM ultrasonic vibration pulses to a vibration origin, and the transmission of ultrasonic detection pulses and the receipt of echo signals from the motion detection point occurs under the control of the digital controller 19 of the ultrasound system 22A.

As indicated by process block 230, at a first distance R between the vibration origin and a first motion detection point, a harmonic signal is detected and its phase $\phi$1 measured, using the techniques described above. In a preferred embodiment, approximately five modulation cycles are required to allow for appropriate detection of the harmonic motion at a motion detection point.

As indicated by process block 232, at a second distance R+Δr between the vibration origin and a second motion detection point, a harmonic signal is detected and its phase φ2 is also measured. In one embodiment, this step is performed after the previous step. However, in other embodiments, depending on length of the off interval of the vibration pulses, it may be possible to obtain more than one phase measurement during the five or so modulation cycles required to impart and detect the harmonic motion of the shear wave.

As indicated by process block 234, the shear wave speed is calculated using Equation (37) for the prescribed modulation frequency.

As indicated by process block 236, the digital controller determines whether the last frequency has been measured. If not, at process block 238, another frequency is selected and process blocks 228-234 are repeated at each desired prescribed frequency. For example, in a preferred embodiment the shear wave speeds are calculated using a set of modulation frequencies including 100 Hz, 200 Hz, 300 Hz, 400 Hz and 500 Hz.

In general, it is desirable to measure the frequency dispersion of the shear wave propagation speed over a wide frequency range because the fit to a dispersion model such as the Voigt model over more frequencies should give a more accurate estimation of elasticity and viscosity. However, there are some limitations as how far the frequency range can be increased. Specifically, tissue response (i.e., the vibration magnitude) decreases when the excitation frequency increases. As the ultrasound radiation force used to excite the studied tissue is fairly small, this will put an upper limit on how high the vibration frequency can go. Also, there is a lower limit on the frequency range due to consideration of ultrasound application time and data acquisition time. As previously stated, the tissue vibration is monitored over several shear wave cycles. If the prescribed frequency is very low, then the high intensity ultrasound needed for vibrating the tissue would have to last for a longer period of time, which may raise concerns about heating both within the studied tissue and at the surface of the ultrasound transducer. Also, the data acquisition time for ultrasound motion detection has to increase accordingly, which can introduce new challenges such as body motion during the data collection, etc. Thus, a frequency range from 100 to 500 Hz has been found to be optimal.

Using the steps described above, data acquisition time can be estimated as follows, assuming that the tissue is vibrated for at least 5 modulation cycles for vibration phase measurement. Five cycles at frequencies of 100, 200, 300, 400 and 500 Hz respectively require vibration times of 50, 25, 17, 13, and 10 ms, which adds up to 115 ms. If phase is measured at two location points for each frequency, the total measurement time will be 230 ms.

As indicated at process block 240, once a shear wave speed is calculated for each frequency in the set of prescribed frequencies, the mechanical property is calculated. For example, the Voigt model can be used as described above to determine the shear elasticity and the shear viscosity of the subject tissue.

In other embodiments, rather than measuring a phase difference and using the Voigt model, an amplitude could be measured and the change in amplitude over distance could be determined and used in conjunction with an appropriate model to determine one or more mechanical properties of the subject target tissue.

Figure 8:
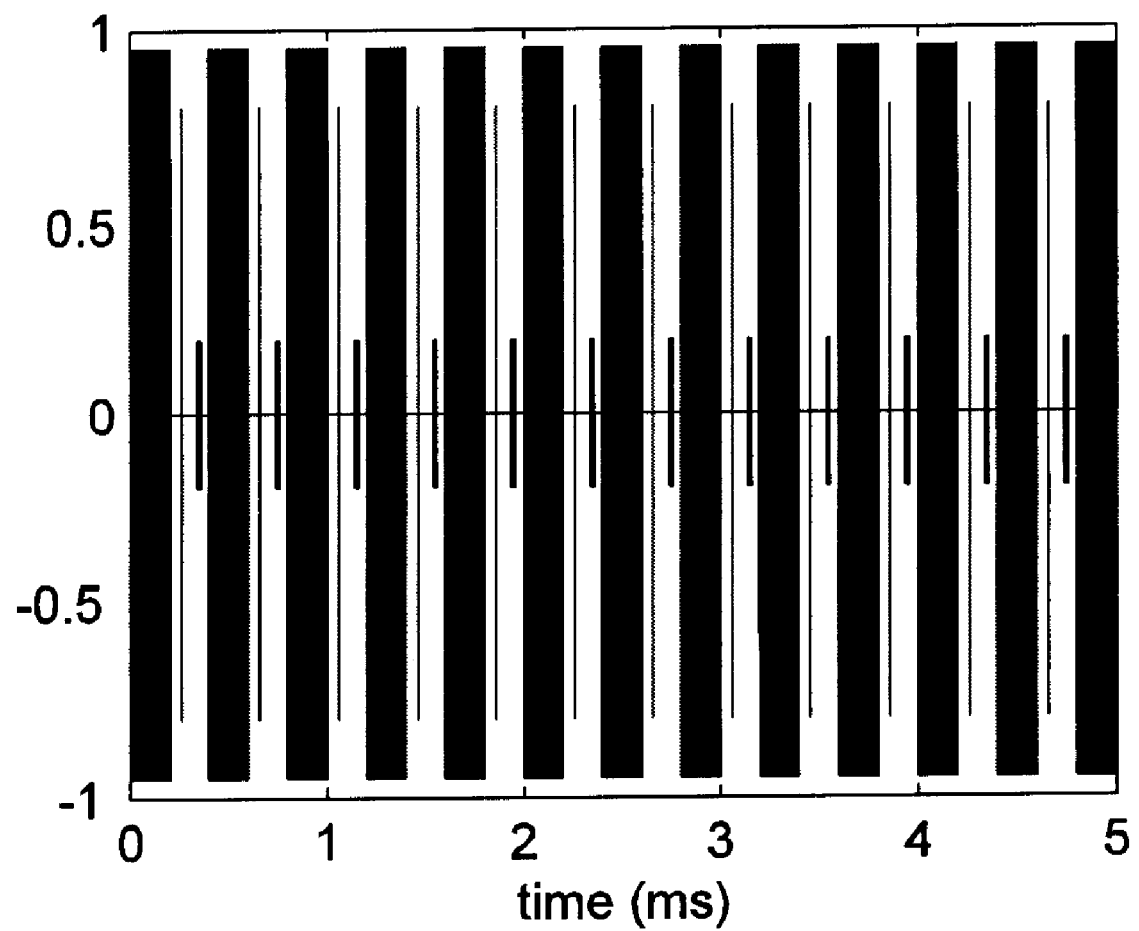
FIG. 8 is a timing diagram of signals transmitted and received by the ultrasound system illustrated in FIG. 5 using two beams having a beat frequency for vibrating the tissue.

FIG. 8 is a timing diagram of signals transmitted and received by the ultrasound system illustrated in FIG. 5 using two beams having a beat frequency for vibrating the tissue. The two beams can be achieved by dividing the elements of the transducer array into two groups and using the first group to transmit ultrasonic pulses at a first frequency and the second group to transmit ultrasonic pulses at a second frequency. For example, the first frequency may be 1 MHz+100 Hz and the second frequency may be 1 MHz−100 Hz. As previously described, such a dual beam will vibrate the tissue at the difference frequency, which in this example is 200 Hz. The same concept of intermittent vibration and detection can be used to measure a characteristic of an imparted shear wave in order to characterize a mechanical property of a subject.

Various transducer types can be used for the ultrasonic virtual biopsy techniques described herein. Because the elements of a linear array are of the order of a wavelength in width, producing beams at a large angle relative to the normal to the transducer face creates grating lobes and also causes a decrease in amplitude because of the beam shape associated with large elements. Therefore the best approach for using linear arrays is to use AM modulated ultrasound while running the array in its normal mode, which is to produce a beam orthogonal to the array surface. A less optimal approach is to excite say, even elements with one ultrasound frequency and odd elements with another frequency. At the focus a beat at the difference frequency will be produced. This method is very similar to the AM modulation method but is not as efficient because the beam does not turn completely off and on.

Phased arrays have elements of the order of less that one half a wavelength. Therefore they can focus at large angles from the surface of the array. Using AM modulation for ultrasonic virtual biopsy with a phased array is similar to that of the linear array. However it is much easier to use the phased array for confocal functions. The reason is that the aperture can be divided into two or more sub-arrays that can focus at relatively large angles. This allows the joint focus to be located anywhere laterally along the focal line in the tissue. However, the AM modulation method is still more efficient at producing motion than the confocal method.

Figures 9A, 9B:
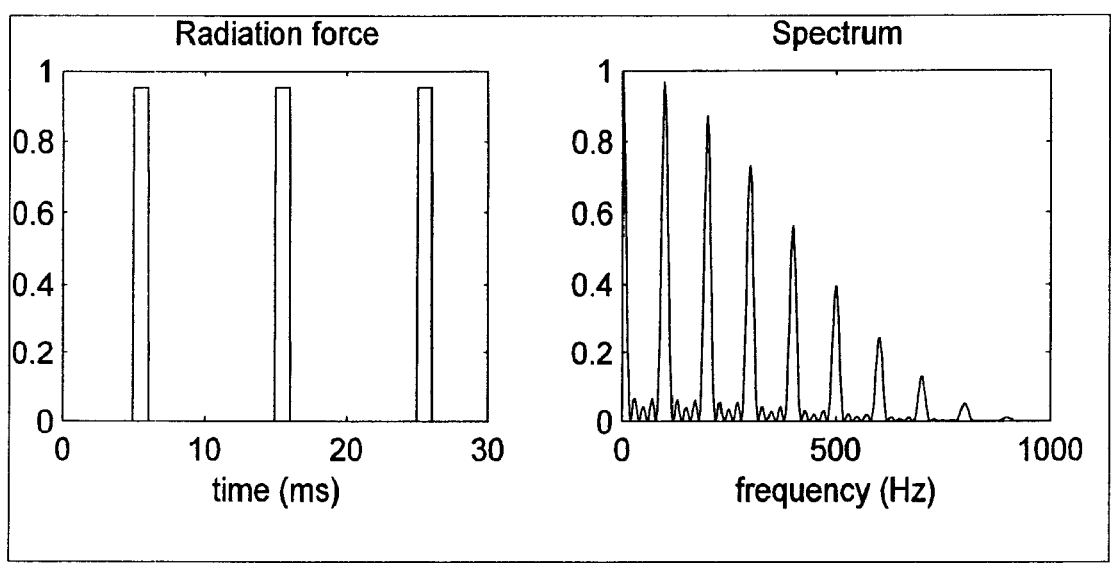
FIG. 9(*a*) is timing diagram of the radiation force generated using tone bursts of ultrasonic pulses and FIG. 9(*b*) illustrates frequency components of the force signal.

Another way to vibrate tissue at one or more prescribed frequencies is by using tone bursts of ultrasonic pulses. The tone bursts are not modulated but have a specific amplitude, duration and period such that they impart a force having desired frequency components. For example, using tone bursts of ultrasonic pulses having a duration of 1 ms and repeated every 10 ms will generate a radiation force such as that illustrated in FIG. 9(a). As shown in FIG. 9(b), this force includes frequency components at a fundamental frequency and multiples thereof, which in this example includes frequencies at 100 Hz, 200 Hz, 300 Hz, 400 Hz and 500 Hz. Using such a waveform for vibration provides advantages in faster data acquisition as described below as well as in lower tissue and transducer heating.

Figure 10:
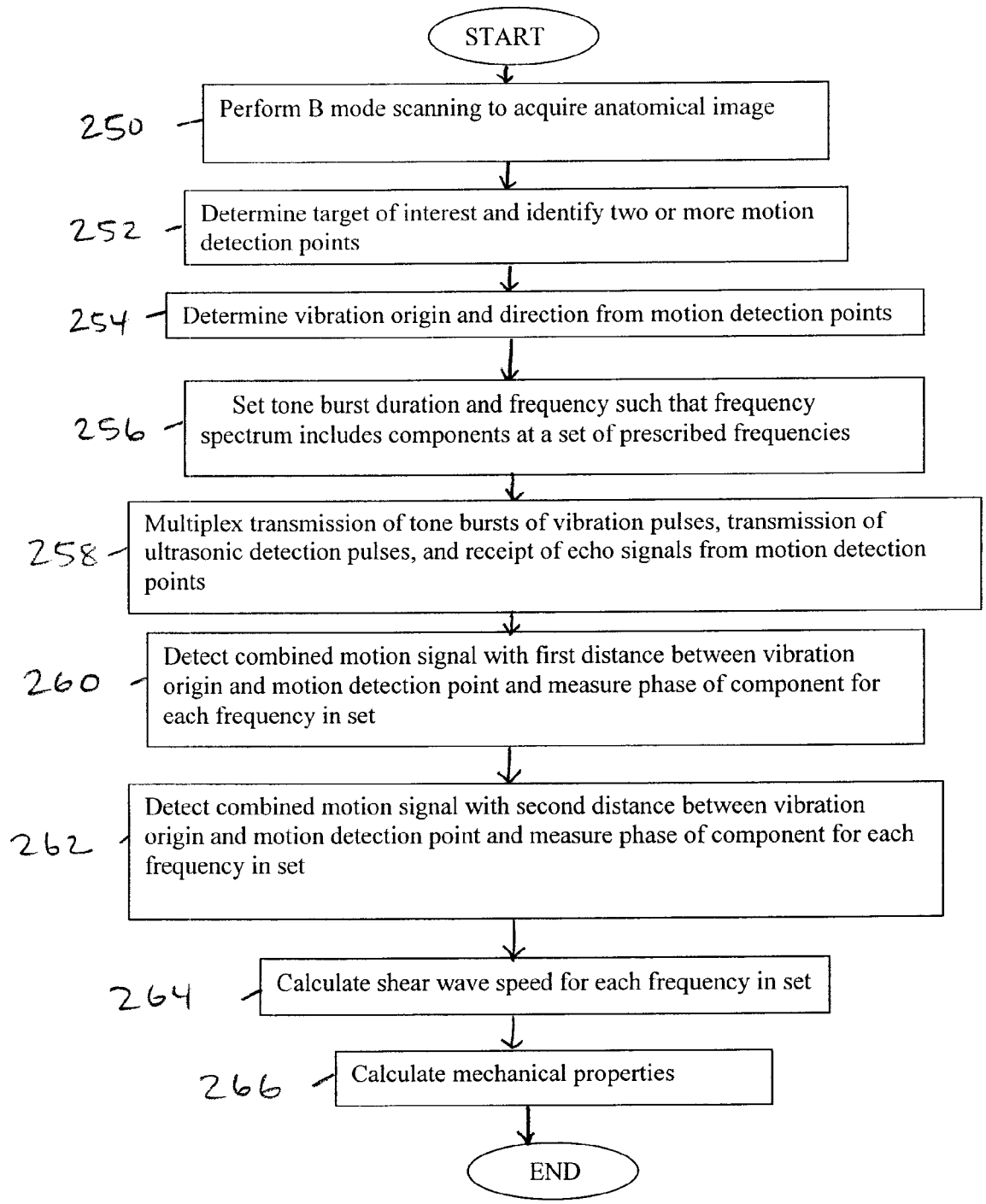
FIG. 10 is a flow chart of steps performed by the ultrasound imaging system of FIG. 5 for measuring mechanical properties of tissue such as shear elasticity and shear viscosity using a shear wave speed dispersion technique and tone bursts of ultrasonic pulses for vibrating the tissue.

FIG. 10 is a flow chart for measuring mechanical properties such as shear elasticity and shear viscosity of subject tissue using a shear wave dispersion technique and tone bursts of ultrasonic pulses. This method is similar to that illustrated in FIG. 7 but does not require repeating the measurement over different frequencies since the tone bursts include frequency components at multiple frequencies. These tone bursts are also easier to implement using a conventional ultrasound system and the average intensity and power would be lower as compared to for example a similar gated AM modulation method. Further, because the off interval is longer (9 msec in the example), the detection pulses can be steered to more than one motion detection point during the off intervals.

In particular, as indicated at process block 250, the ultrasound system is operated using B mode scanning to acquire an anatomical ultrasound image of a region of interest, such as the liver. As indicated at process block 252, a target of interest is determined such as by identifying in the ultrasound image two or more motion detection points at which it is desired to obtain the mechanical properties, assuming that the tissue is approximately homogenous at these two points. As indicated at process block 254, a vibration origin is also determined by determining a distance R between it and one of the motion detection points, with a distance of R+Δr between it and the other motion detection point, and with the vibration origin and the two or more motion detection points being co-linear.

As indicated at process block 256, the tone burst duration and frequency (or period) are determined such that the frequency spectrum of the radiated force includes components at a set of prescribed frequencies. For example, in one embodiment, the duration is 1 ms and the tone bursts are repeated every 10 ms, and the set of prescribed frequencies includes 100 Hz, 200 Hz, 300 Hz, 400 Hz and 500 Hz. It may also be desirable however for the repetition frequency to be varied as needed to avoid interference between the pushing pulses and the detection pulses. For example, using a repetition frequency of the pulse echo ultrasound of 2.5 kHz, the tissue can be excited at 156.25 Hz, and from this a single set of vibration data including shear wave speeds at 156.25 Hz, 312.5 Hz, 468.75 Hz, and 600 Hz can then be determined.

As indicated at process block 258, the transmission of the intermittent AM ultrasonic vibration pulses to a vibration origin, and the transmission of ultrasonic detection pulses to and the receipt of echo signals from the first motion detection point and the second motion detection point occurs.

As indicated at process block 260, at a first distance R between the vibration origin and the first motion detection point, a combined motion signal is detected and the phase of a component at each frequency in the set of frequencies is measured, using the techniques previously described herein.

As indicated at process block 262, at a second distance R+Δr between the vibration origin and the second motion detection point a combined motion signal is detected and the phase of a component at each frequency in the set of frequencies is measured.

Because the length of the off interval of the vibration pulses in this example is 9 ms, it is possible for process blocks 260 and 262 to occur during the same approximately five tone burst cycles required to detect and measure phases of the harmonic combined motion signal.

As indicated at process block 264, the shear wave speed is calculated using Equation (37) for each frequency in the set of prescribed frequencies.

As indicated at process block 266, the mechanical property is calculated. For example, the Voigt model can be used as described above to determine the shear elasticity and the shear viscosity of the subject tissue, and in this manner, a virtual biopsy is performed.

Figure 11:
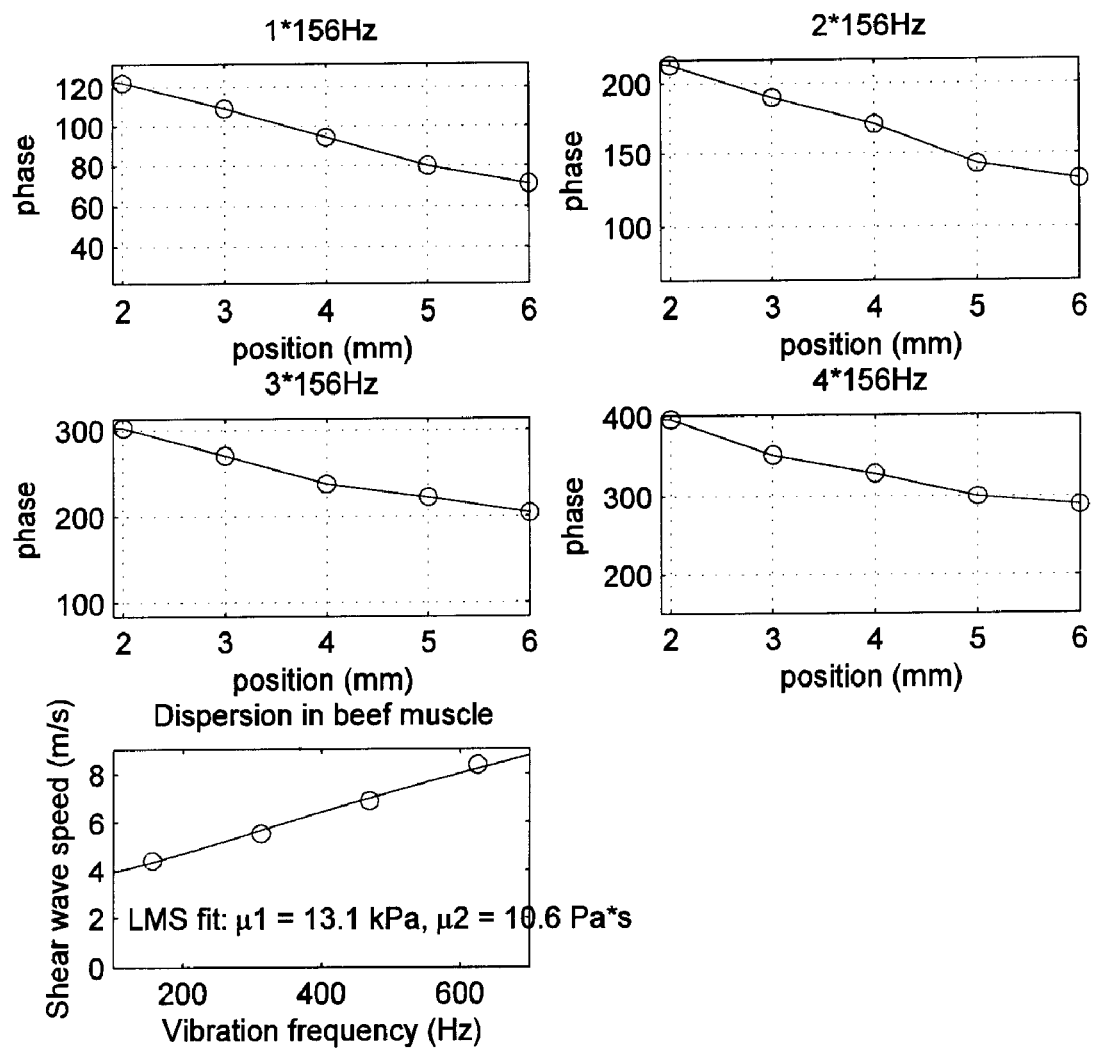
FIG. 11 is an example showing data obtained using the method of FIG. 10.

FIG. 11 illustrates an example of data obtained using tone burst type excitation using a harmonic frequency of 156 Hz.

To summarize, there are many advantages of the use of tone bursts. This method is very easy to implement in a commercial ultrasound scanner and the data acquisition times are fast, e.g., below tens of milliseconds. Further, lower average ultrasound power and lower total energy translate to a reduction in tissue and transducer heating. The accuracy that can be obtained is comparable to the gated AM excitation method.

Other embodiments of the invention are also possible. For example, an ultrasound system can be used for excitation in a manner such as described herein, and other known means, such as MRI or optical methods, can be used to detect the ultrasound motion.

The invention claimed is:

1. A method for measuring a mechanical property of a subject, the method comprising:
 a) applying ultrasonic vibration pulses using an ultrasonic transducer to a vibration origin in the subject in an on-off time sequence in order to impart a harmonic motion at a prescribed frequency to the subject, the harmonic motion propagating outward from the vibration origin;
 b) applying ultrasonic detection pulses to a motion detection point, which is a selected distance away from the vibration origin, and receiving echo signals therefrom using the same transducer when the vibration pulses are off, in order to sense the harmonic motion propagating outward from the vibration origin at the motion detection point;
 c) detecting a harmonic signal at the prescribed frequency in the received echo signals;
 d) measuring a characteristic of the detected harmonic signal; and
 e) calculating the mechanical property using the measured characteristic.

2. The method as recited in claim 1 wherein the on sequence of vibration pulses is a gated amplitude modulated signal having a modulation frequency at the prescribed frequency.

3. The method as recited in claim 1 wherein the on sequence of vibration pulses is a series of tone bursts repeated at the prescribed frequency.

4. The method as recited in claim 3 wherein the tone bursts include frequency components at the prescribed frequency and harmonics thereof.

5. The method as recited in claim 1 wherein the transducer includes a plurality of transducer elements and the on sequence of vibration pulses is produced by simultaneously transmitting pulses at a first frequency using a first group of transducer elements and transmitting pulses at a second frequency using a second group of transducer elements, and the difference between the two frequencies is the prescribed frequency.

6. The method as recited in claim 1 wherein the measured characteristic is at least one of amplitude and phase.

7. The method of claim 1 in which steps a) through d) are repeated using a second motion detection point to produce a second measured characteristic and the mechanical property is calculated in step e) using both of said measured characteristics.

8. The method as recited in claim 1 in which steps a) through d) are repeated at each of a set of prescribed frequencies, and the mechanical property is calculated in step e) using all of the measured characteristics.

9. The method as recited in claim 1 in which steps c) and d) include:
 i) demodulating the received echo signals to produce quadrature I and Q signals;
 ii) calculating the arctangent of the ratio of said I and Q signals; and
 iii) filtering the signal which results from step ii) to detect a harmonic signal therein at the prescribed frequency.

10. A method for measuring a mechanical property of a subject, the method comprising:

a) applying ultrasonic vibration pulses using an ultrasonic transducer to a vibration origin in the subject in an on-off time sequence in order to impart harmonic motion to the subject at each of a set of prescribed frequencies;

b) applying ultrasonic detection pulses to the subject and receiving echo signals therefrom using the same ultrasonic transducer when the vibration pulses are off, and obtaining such echo signals at each frequency in the set using a first distance between a motion detection point and the vibration origin and a second distance between a motion detection point and the vibration origin, c) detecting a harmonic first signal in the echo signals associated with the first distance and detecting a harmonic second signal in the echo signals associated with the second distance for each frequency in the set;

d) measuring a phase of the harmonic first signal and a phase of the harmonic second signal and determining the phase difference between the two phases for each frequency in the set;

e) calculating a wave speed using the determined phase difference and a difference between the first distance and the second distance for each frequency in the set, thereby obtaining wave speed dispersion information; and f) calculating a mechanical property from the wave speed dispersion information.

11. The method as recited in claim 10 wherein at least two frequencies in the set are applied to the subject at a different time than the other frequencies in the set.

12. The method as recited in claim 10 wherein each frequency in the set is applied to the subject at the same time as the others frequencies in the set.

13. The method as recited in claim 10 wherein the detection pulses are applied to a first motion detection point during the same off interval that detection pulses are applied to a second motion detection point.

14. The method as recited in claim 10 wherein the detection pulses are applied to a first detection point during different off intervals than detection pulses are applied to a second detection point.

15. The method as recited in claim 10 wherein the on sequence of vibration pulses is a gated amplitude modulated signal having a modulation frequency.

16. The method as recited in claim 10 wherein the on sequence of vibration pulses is a series of tone bursts repeated at the prescribed frequency.

17. The method as recited in claim 16 wherein the tone bursts include frequency components at the prescribed frequency and harmonics thereof.

18. The method as recited in claim 10 wherein the transducer includes a plurality of transducer elements and the on sequence of vibration pulses is produced by simultaneously transmitting pulses at a first frequency using a first group of transducer elements and transmitting pulses at a second frequency using a second group of transducer elements, and the difference between the two frequencies is the prescribed frequency.

19. The method as recited in claim 10 in which steps c) and d) includes:
   i) demodulating the received echo signals to produce quadrature I and Q signals;
   ii) calculating the arctangent of the ratio of said I and Q signals; and
   iii) filtering the signal which results from step ii) to detect a harmonic signal therein at the prescribed frequency.

* * * * *